United States Patent [19]

Moss, III

[11] 4,143,765
[45] Mar. 13, 1979

[54] SHIPPER TRAY FOR TISSUE CULTURE DISHES

[76] Inventor: L. Howard Moss, III, 5236 Vernadale St., Dayton, Ohio 45429

[21] Appl. No.: 762,399

[22] Filed: Jan. 26, 1977

[51] Int. Cl.$^2$ .............................................. B65D 85/62
[52] U.S. Cl. .................................. 206/445; 206/0.83; 206/0.84; 211/78
[58] Field of Search ............... 206/526, 445, 0.8, 0.81, 206/0.82, 0.83, 0.84; 220/20, 21; 211/78

[56] References Cited

U.S. PATENT DOCUMENTS

| | | | |
|---|---|---|---|
| 1,095,256 | 5/1914 | Willis | 206/0.84 |
| 1,151,483 | 10/1924 | Kusel | 206/0.83 |
| 3,139,977 | 7/1964 | Burdick | 206/0.83 |
| 3,592,204 | 7/1971 | Hernandez | 206/0.84 |
| 3,972,419 | 8/1976 | Short | 211/78 |

FOREIGN PATENT DOCUMENTS 1089642  3/1955  France ..................................... 206/0.84

*Primary Examiner*—William Price
*Assistant Examiner*—Joseph Man-Fu Moy

[57] ABSTRACT

A convenient shipper and display tray for a plurality of tissue culture dishes comprising a principal body having a plurality of spaced side-by-side vertical voids adapted to receive said dishes in vertical stacked array and finger slots communicating from the exterior of said body to the vertical stacked array, accommodating finger movement and removal of dishes stacked therein and desirably inclusive of spill containment means and sterile covering means for each of said stacks as well as provisions for removability thereof.

6 Claims, 4 Drawing Figures

SHIPPER TRAY FOR TISSUE CULTURE DISHES

The present invention relates to a convenience shipping container and dispenser tray structure for a plurality of tissue culture dishes; said dishes being composed of a relatively flat circular cup-like receptacle or container and a cover featuring a depending skirt loosely fitting about said flat container.

More to the point, the present invention contemplates such a structure of multi-faceted convenience in that the container or tray as hereinafter described is useful for shipping a relatively large plurality of the tissue culture dishes; is adapted in so doing to hold and transport these tissue culture dishes in safety and in isolated sterile condition; and, lastly, serves as a convenience display and dispenser tray of significant usefulness at the point of use by the consumer.

The tissue culture dishes as above described are usually formed of glass or a plastic such as methyl methacrylate and are employed in the field of medicine, bacteriology, biology, chemistry and science generally for the containment of various tissue cultures for any desired or proscribed period of time as to permit exposure of the tissue culture to any one of a variety of controlled environments; following which, comparative testing, observation and analysis of the tissue culture can be performed by the experimenter. FIG. 4 of the present drawings is a side elevation view of such a dish. Tissue culture dishes presently are marketed in rather loosely packaged plastic sleeves formed of a flexible film material such as polyethylene. Shipping in this fashion leads to breakage of the rather frangible and fragile dishes, whether made of plastic or glass. The sleeves or tubes of flexible polyethylene, once opened, immediately expose the tissue culture dishes to the random environmental conditions present at the lab table or wherever opened. The dishes in each flexible shipping tube may number from 20 or so upward; which number, upon destruction of the flexible tube or sleeve, must be promptly handled and stored for use. This can usually be on a shelf or in a drawer, where again random conditions prevail, which certainly may include contaminating and unsterile conditions, even though the dishes do include a cover. Such is due to the fact, of course, that the cover is rather loose fitting. However, over and above this, the handling incident to storage of such a large plurality of these dishes becomes a cumbersome task. Further, the covers are so loose fitting that any movement or shifting by hand manipulation will frequently cause the cover to come off at the base such that the sterile conditions are destroyed and otherwise leading to contamination and, of course, unreliable results in their ultimate usage as a storage container for a particular tissue culture specimen.

Since the tissue culture dishes are used for a scientific purpose, sterility and, as well, general absence of contamination is quite important along with cleanliness which lead to accuracy and consistency. These are factors, of course, which are desirably maintained at high level to insure the reliability of the testing and the observation involved in the particular experimentation, such as exposure to incubation conditions or the like. Lack of sterility, cleanliness and the other factors adversely affect the culture and/or the culture medium and in turn adversely affect the reliability of the comparative testing, observation, analysis and the like.

It is also observed that the handling of the large number of tissue culture dishes, whether they be of the smaller 35 × 10 millimeter style or the larger 60 × 15 millimeter style, is beset with difficulties in the sense of the large numbers that must be individually handled, including the removal of the cover, the introduction of the culture and the replacement of the lid and then the setting down for further filling of other dishes. In other words, the handling of these dishes in large numbers presents quite a problem in handling and logistics, particularly compounded by the fact that the use may desirably entail movement from one location to several different locations within the laboratory or the particular situs of use. The handling of the dishes in use frequently results in spillage, cross-contamination and consequent inaccurate results.

With the above introduction, it is an object of the present invention to provide a receptacle/tray structure which significantly overcomes the problems and difficulties above described as normally encountered in the shipping and use of the tissue culture dishes.

It is a particular object of the present invention to provide a receptacle/tray which is adapted to safely contain a plurality of tissue culture dishes in a relatively protected and shock-resistant enclosure.

It is still another object of the present invention to provide such a receptacle/tray structure which is relatively lightweight and is constructed as to permit visualization of the dishes.

It is yet another object of the present invention to provide such a structure which holds such dishes in an orderly proscribed manner and particularly in such a manner as will lend itself to achieving a sterile environment and the maintenance of the sterility during shipping.

It is a further object of the present invention to provide such a receptacle/tray which is of relatively simple construction and is adapted to be formed by a variety of plastic molding techniques, thereby involving a relatively low unit cost as to be economically attractive.

It is still another object of the present invention to provide such a receptacle/tray which is of significant utility following shipment in serving as a convenience tray for a large plurality of the dishes in orderly, proscribed and visually attractive manner, as well as reduced spillage and errors incident thereto.

The foregoing as well as other objects of the present invention will become apparent to those skilled in the art from the following detailed description taken in conjunction with the annexed sheets of drawings on which there are presented, for purpose of illustration only, several embodiments of the present invention.

IN THE DRAWINGS

Figure 1:
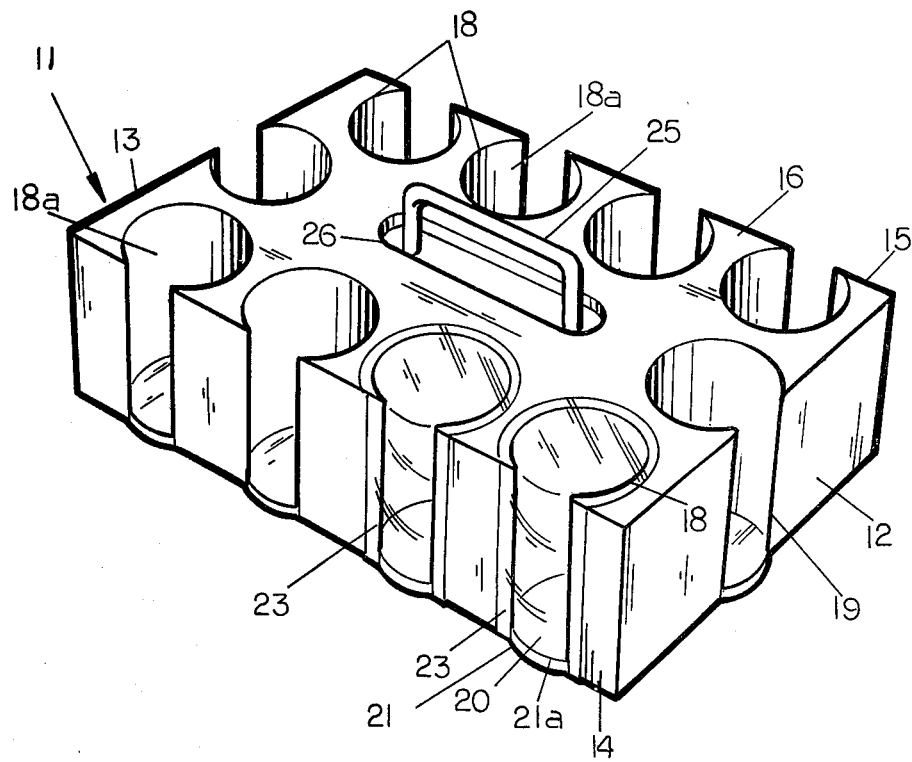
FIG. 1 is a three-quarter perspective view of a receptacle/tray in accordance with one embodiment of the present invention.

Considered most basically, the present invention envisions a principal body member formed of transparent material and inclusive of a plurality of vertically spaced voids or columns adapted to easily receive and contain a vertical stack of tissue culture dishes with separate slot means in the body communicating independently with each of the voids or columns as to permit finger manipulation insertion and removal of the dishes and, most desirably, an individual cover embracing the slots and columns or voids as to create a sterile isolated chamber for a given plurality of the dishes.

Referring now more specifically to the drawings, there is disclosed a receptacle/tray 11 in accordance with the present invention. The tray is an elongate, generally hollow, rectangular member having a front wall 12, a rear wall 13 in parallel spaced disposition and spaced parallel side walls 14 and 15 and, as well, a top wall 16. A plurality of circular voids or columns 18 are provided and are so disposed that the voids intersect the adjacent wall surface to leave a vertical slot opening 19. Each of the voids or columns 18 terminate at its lower extremity with a circular bottom wall 20 which extends beyond the vertical surface of its associated side wall, as at 21, and this extension includes an upstanding vertical lip 21a which extends in semicircular fashion to sealingly join the adjacent side wall. Reference numeral 23 identifies a flexible sheet-like cover which extends from the lip 21a vertically up the side wall 14 and thence across the top wall in surrounding or covering relationship with the horizontal opening coincident with the void or column 18. For purpose of illustration, several of the voids 18 are shown covered by paper seals 23, with the remainder shown with no cover or seal.

Projecting upwardly from the top wall 16 is a handle 25 which is surrounded by a recessed region 26, with the handle being vertically lowerable down into the recessed region but being shown in its upper extended position for convenient grasping by the hand of the user. Although not shown, the interior of the member 11 is essentially hollow, excepting for the bottom wall 20 for each of the voids or columns and the generally circular side wall 18a of each of the columns. These side walls 18a are desirably relatively thin, in the neighborhood of ⅛ inch or less, and the entire structure is desirably molded of a relatively inexpensive and relatively lightweight plastic material. Most preferably, the tray device is formed of a plastic such as methyl methacrylate or polyvinyl chloride or the like which are inherently clear and would result in a structure which, in the form as shown in FIG. 1, would be relatively transparent from whatever position achieved. The structure is desirably formed by molding in any manner known to the art. Excepting for the handle, the structure can be molded in one piece by injection and/or compression molding. Alternatively, the structure may be molded in several pieces which are then joined by heat, adhesive or the like. The bottom wall extension and upstanding lip 21a, in cooperation with the side wall 18a, serve to provide a leak-proof reservoir for any spillage that might occur and thus enhance the housekeeping attendant to the utilization of the device in the laboratory for transporting tissue culture dishes containing various medium in the transportation about the laboratory into and out of autoclaves and the like.

In accordance with an alternative or modification of the present invention, the cylindrical side wall 18a may be dispensed with in favor of several vertical strut members in spaced parallel array; said strut members in aggregate defining the generally cylindrical reservoir column or void 18 for reception of a plurality of vertically stacked tissue culture dishes. In this embodiment, the struts may extend the vertical extent of the column to augment the lightweight nature and accordingly such structure would require less plastic, which would further lower costs. The structure can, of course, be designed to include the struts as just described but still incorporate a cylindrical continuous wall in the lower regions of the void or column for a height equal to the height of the lip 21a so as to retain the leak-proof or spill-resistant reservoir to enhance the housekeeping aspects of the tray device. Neither the molding operation nor the choice of the material of construction for the particular receptacle/tray form any real part of the present invention and accordingly whether molded in one piece or in several pieces, followed by a fusion or adhesive bonding, is relatively immaterial. Certainly, the intricate configuration of the device would suggest that the tray device 11 might well be molded more economically in several pieces, with a later adhesive or heat-fusion of the several pieces into the configuration as shown in FIG. 1. The handle device, of course, is separate, as are the paper covers 23. These covers may be formed of paper cut to an appropriate pattern as to fit the tray structure as shown, with application and securement being by adhesive. The covers 23 may also be preformed in a two-sheet strip-like structure with the backing removable to reveal the cover already bearing an adhesive for ready securement to the margins of the voids 18. The individual covers allow the sterile conditions to be retained in individual column or void reservoirs containing a stack of the tissue culture dishes. Desirably, in accordance with preferred embodiments of the present invention, the covers 23 are formed of transparent film-like materials such as polyethylene. The tray structure 11 may, of course, be formed of stronger plastic materials such as the amine-aldehyde condensation products or the so-called "ABS" polymers formed of acrylonitrile, butadiene and styrene.

Figure 4:
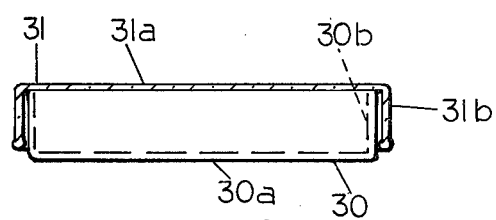
FIG. 4 is a side elevation view of a tissue culture dish of the type contained, shipped and displayed in the receptacle/tray of the present invention.

The tissue culture dish for which the receptacle/tray of the present invention is designed as a shipper, carrier and laboratory convenience rack is shown in FIG. 4 and, as can be seen, is composed of a generally cylindrical cup-like member having a bottom wall 30a, a cylindrical upstanding continuous side wall 30b, a separate cover 31 having a cylindrical top wall 31a and a marginal depending skirt 31b which telescopes somewhat loosely down about the upstanding wall 30b of the dish. These dishes and cover combinations are usually formed of a transparent plastic, usually methyl methacrylate as indicated hereinabove. A plurality of the dish and cover assemblies are conveniently stacked in vertical array in each of the columns or voids 18 of the receptacle/tray member 11. The height of the structure, principally its side walls, can be selected and molded to accommodate a given number of the dishes and, of course, the overall size of the device can be selected to meet the diameter of the cover dish. The structure as shown can be seen to include 10 columns or voids which could each easily accommodate 10 vertically stacked dishes as described to give an overall capacity of the structure of 100 dishes. Such a package is eminently, of course, more desirable for shipping purposes than the present shipping in flexible tubular polyethylene bags.

It will be appreciated that the slots 19 and the opening in the top wall permit very easy movement finger manipulation of the individual or plurality of culture dishes upward and out of the tray device for use as needed. Similarly, the tissue culture dishes may be reintroduced into the tray in a convenient and orderly manner once the particular culture medium desired for the particular experimentation or work has been located in the dish and further transportation and/or storage is desired.

Figure 3:
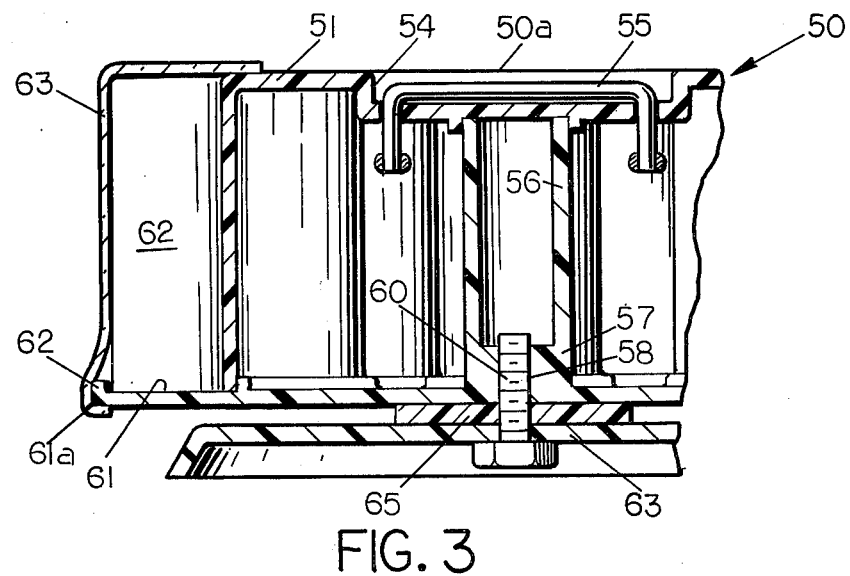
FIG. 3 is a sectional view taken on the line 3—3 of FIG. 2.
Figure 2:
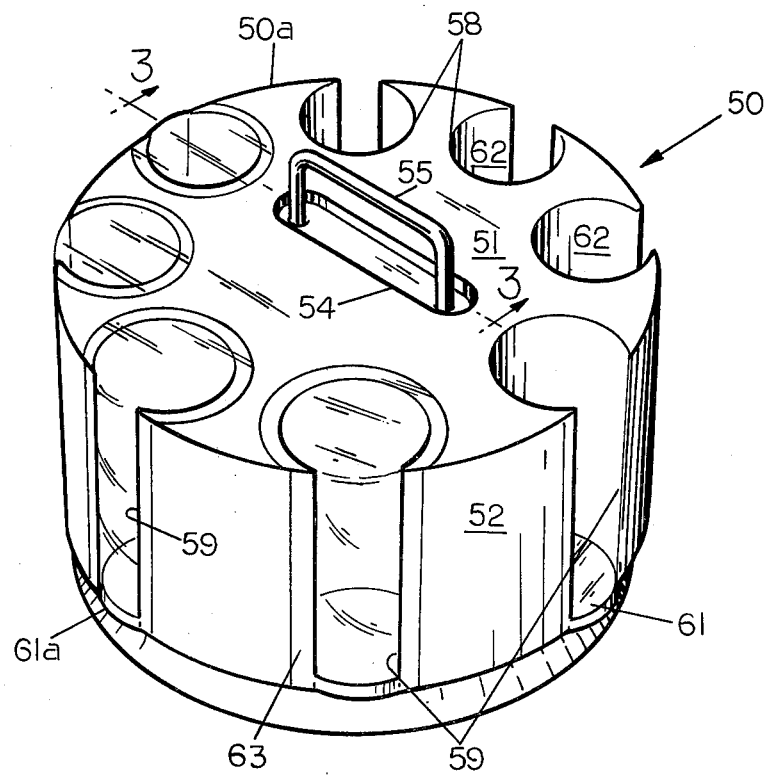
FIG. 2 is a three-quarter perspective view of a receptacle/tray of the present invention and embodying features of structure in accordance with a further embodiment of the present invention.

A receptacle/tray 50 in accordance with an alternative embodiment of the present invention is shown in FIGS. 2 and 3. In this embodiment, the structure is generally cylindrical and having a horizontal section which is circular as shown and includes a principal body member 50a having a horizontal top wall 51 and an outer cylindrical wall 52 and is provided with a plurality of vertical void or column reservoirs 58 which are situated in radial disposition around the outer surface, with the voids intersecting therewith to provide for each void or column a corresponding vertical slot 59. Each column or void has, at its lower terminus, a bottom wall 61 bounded by the cylindrical wall surface defining the column or void and identified by the reference numeral 62. The bottom wall segment 61 for each of the columns or voids projects outwardly beyond the cylindrical outer wall, as shown in FIG. 3 at 61a, and terminates in a slightly upstanding or upturned lip 62 which, in conjunction with the bottom wall, provides a spillage guard or shield. In accordance with preferred objectives of the present invention, a paper on polyethylene seal cover 63, similar to the cover 23 in the embodiment of FIG. 1, is provided and such is shown secured in place on several of the voids or columns 59. The top wall of the member 50a identified by the reference numeral 51 includes a recess 54 in which is mounted a vertically reciprocable or movable handle 55. Centrally of the member 50a is a hollow sleeve 56 terminating in a lower thickened section 57 which is bored as at 58 to receive an upstanding stud 60 mounted in an inverted saucer-like base 63 and having therebetween a washer 65 to allow a rotation or carousel movement of the body 50a to enhance the display and convenience function.

The body 50a can be formed of the same materials of construction as described in conjunction with the member 11 in FIG. 1 and may similarly be formed by molding as a single piece or in several pieces to be later cemented, adhered or heat-fused together, depending upon the economies of the particular design employed. The embodiment of FIGS. 2 and 3 is shown with the columns or voids 59 defined by a continuous cylindrical wall surface 62. It will be appreciated that the reservoir for the stacked array of flat tissue culture dishes may be defined by a plurality of spaced ribs or struts instead of the continuous smooth wall as indicated. In a manner similar to that of the previous embodiment, the receptacle/tray 50 is conveniently filled with sterile tissue culture dishes, followed by establishment of sterile conditions in the individual column or void reservoirs in a known manner. The strip of paper or polyethylene precut sheet can then be applied in the manner shown to create a completely sterile environment for the individual stacked array of dishes. The strips may be left on during shipment, of course, to insure maintenance of the sterile conditions for the dishes and thereafter. Finally, in the laboratory, for example, the individual stacks can be made available by simply peeling away the strip or seal as needed to reveal the needed stacked array of dishes available for finger lifting and removal in the manner similar to that of the previous embodiment.

The foregoing disclosure and the accompanying drawings, when evaluated by the person skilled in the art, will suggest a variety of obvious modifications that may be made in or incorporated into the structure as shown and described and all such obvious modifications, changes and adaptations are intended to be included within the scope of the present invention unless such would do violence to the language of the appended claims.

I claim:

1. A receptacle for convenience shipping, storage and display of a plurality of tissue culture dishes of generally thin configuration, said receptacle comprising a principal body member including a plurality of spaced vertical voids having a horizontal section generally congruent to the configuration of said dishes, said body including a top wall intersected by said voids to define an opening allowing upward movement of dishes in said voids and beyond said opening; said voids intersecting the marginal surface of said body to define vertical slots, accommodating finger manipulation and removal of said dishes, a plurality of dishes located within said voids, and a plurality of removable covers sealing said opening and the vertical slots, to isolate said dishes within their respective chambers as defined by said voids and their respective covers.

2. The invention as claimed in claim 1, wherein said body is a molded plastic of transparent character.

3. The invention as claimed in claim 1, wherein said body includes a plurality of outwardly extending horizontal bottom wall surfaces beneath each void and a connected upstanding lip which conjointly define a leak-proof recess.

4. The invention as claimed in claim 3, which includes a base having an upstanding rotatable means, and said receptacle includes a lower means engageable with said base, rotatable means whereby said body is easily rotatable for viewing of said vertically stacked dishes and said voids.

5. The invention as claimed in claim 1 which includes a base having an upstanding rotatable means, and said receptacle includes a lower means engageable with said base rotatable means whereby said body is easily rotatable for viewing of said vertically stacked dishes in said voids.

6. The invention as claimed in claim 5, wherein said covers are transparent.

* * * * *